United States Patent [19]

VandenBerg

[11] Patent Number: Plant 6,887

[45] Date of Patent: Jun. 27, 1989

[54] CHRYSANTHEMUM PLANT NAMED HADA

[75] Inventor: Cornelis P. VandenBerg, Salinas, Calif.

[73] Assignee: Yoder Brothers, Inc., Barberton, Ohio

[21] Appl. No.: 173,084

[22] Filed: Mar. 25, 1988

[51] Int. Cl.[4] ..... A01H 5/00

[52] U.S. Cl. ..... Plt./80

[58] Field of Search ..... Plt./76, 80

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Hada particularly characterized by its flat capitulum form; decorative capitulum type; red-purple ray floret color; diameter across face of capitulum of up to 62 mm at maturity; uniform eight week photoperiodic flowering response to short days; peduncle length ranging from 10 to 16 cm on open, terminal sprays; medium plant height when grown as a single stem spray cut mum; and excellent tolerance to low temperatures for bud initiation and flower development.

3 Drawing Sheets

The present invention comprises a new and distinct cultivar of Chrysanthemum, botanically known as *Dendranthema grandiflora,* and referred to by the cultivar name Hada.

Hada, identified as 84125004, was originated from a cross made by Cornelius P. VandenBerg in a controlled breeding program in Salinas, Calif. in 1983.

The female parent and the male parent of Hada were both unnamed seedlings, identified respectively as 81822002 and 79C08001.

Hada was discovered and selected as one flowering plant within the progeny of the stated cross by Cornelis P. VandenBerg in August 1984 in a controlled environment in Salinas, Calif.

The first act of asexual reproduction of Hada was accomplished when vegetative cuttings were taken from the initial selection in October 1984 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Hada are firmly fixed and are retained through successive generations of asexual reproduction.

Hada has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice. The low temperature tolerance was determined in repeated flowerings in Bogota, Colombia.

The following traits have been repeatedly observed and are determined to be basic characteristics of Hada, which, in combination, distinguish this Chrysanthemum as a new and distinct cultivar;

1. Flat capitulum form.
2. Decorative capitulum type.
3. Red-purple ray floret color.
4. Diameter across face of capitulum up to 62 mm at maturity.

5. Uniform eight week photoperiodic flowering response to short days.
6. Peduncle length ranging from 10 to 16 cm on open terminal sprays.
7. Medium plant height, requiring two long day weeks prior to short days to attain a flowered plant height of 100 to 110 cm for year-round flowerings.
8. Excellent tolerance to low temperatures for bud initiation and flower development.

The accompanying photographic drawings show typical inflorescence and leaf characteristics of Hada, with the colors being as nearly true as possible with illustrations of this type.

Sheet 1 is a color photograph of Hada grown as a single stem cut spray mum.

Sheet 2 is a black and white photograph of three views of the inflorescence of Hada.

Sheet 3 is a black and white photograph showing the upper and under sides of the leaves of Hada at three stages of development (mature, intermediate and immature).

Of the commercial cultivars known to the inventor, the most similar in comparison to Hada is Beloved, disclosed in U.S. Plant Pat. No. 3,741. Reference is made to Chart A, which compares certain characteristics of Hada to the same characteristics of Beloved.

Similar traits are capitulum form and type, spray formation and plant height. The ray floret color of Beloved is described as lavender; the ray floret color of Hada is red-purple. Hada has a smaller diameter of capitulum, a faster flowering response and a better low temperature tolerance than Beloved.

In the following description, color references are made to The Royal Horticultural Society Colour Chart. The color values were determined on plant material grown in Salinas, Calif. on Oct. 8, 1987.

Classification:

*Botanical.*—*Dendranthema grandiflora,* cv Hada.

*Commercial.*—Decorative cut spray mum.

INFLORESCENCE

A. Capitulum:

*Form.*—Flat.

*Type.*—Decorative.

*Diameter across face.*—Up to 62 mm at maturity.

B. Corolla of ray florets:

*Color (general tonality from a distance of three meters).*—Purple.

*Color (upper surface).*—70D.

*Color (under surface).*—75D.

*Shape.*—Longitudinal axis straight; cross section of ray floret concave; oblong.

C. Corolla of disc florets:

*Color (mature).*—Closest to 6A.

*Color (immature).*—Closest to 144B.

D. Reproductive organs:

*Androecium.*—Present on disc florets only; scant pollen.

*Gynoecium.*—Present on both ray and disc florets.

PLANT

A. General appearance:

*Height.*—Medium; 100 to 110 cm as a single stem cut mum with 2 long day weeks prior to short days.

B. Foliage:

*Color (upper surface).*—147A.

*Color (under surface).*—147B to 147C.

*Shape.*—Lobed and slightly serrated.

CHART A

COMPARISON OF HADA AND BELOVED

| | Hada | Beloved |
|---|---|---|
| Ray floret color | Red-purple | Lavender |
| Capitulum form and type | Flat Decorative | Flat Decorative |
| Spray formation | Terminal 10 to 16 cm peduncles | Terminal 10 to 18 cm pedunces |
| Diameter across face of capitulum | Up to 62 mm | Up to 83 mm |
| Plant height | Medium | Medium |
| Flowering response period | 8 weeks | 9 weeks |
| Low temperature tolerance | Excellent | Marginal |

COMPARISONS MADE OF PLANTS GROWN AS SINGLE STEM SPRAY CUT MUMS IN SALINAS, CALIFORNIA

I claim:

1. A new and distinct Chrysanthemum plant named Hada, as described and illustrated, and parts thereof.

* * * * *

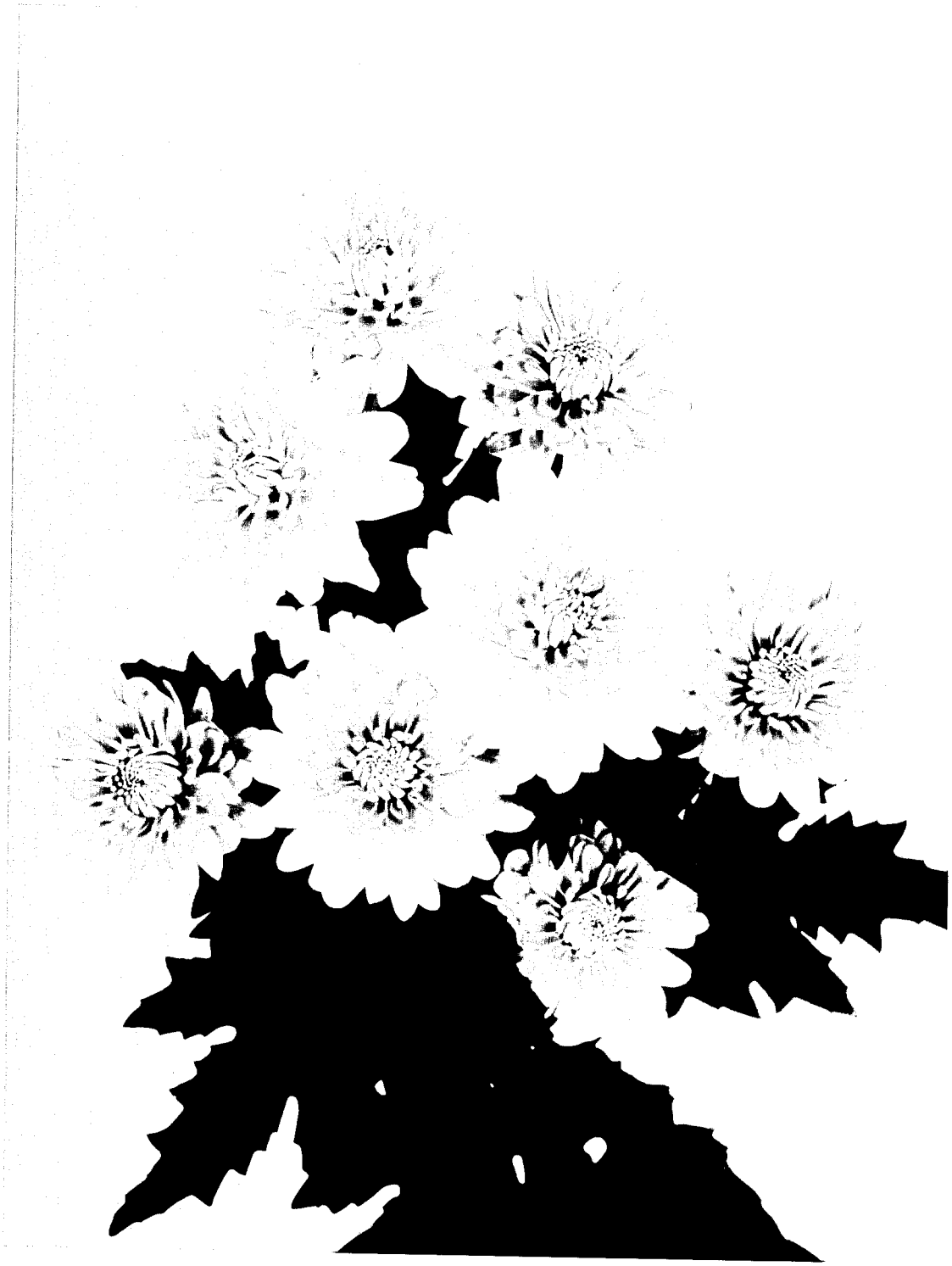

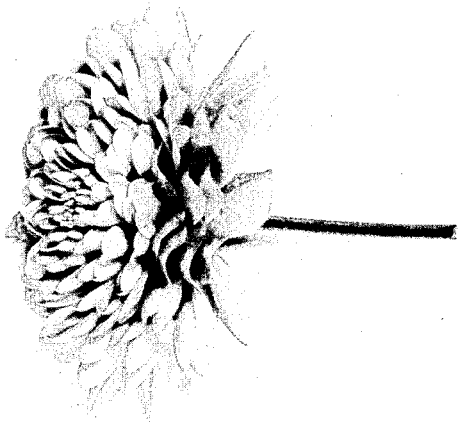
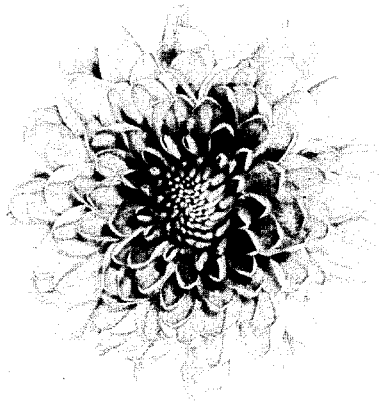
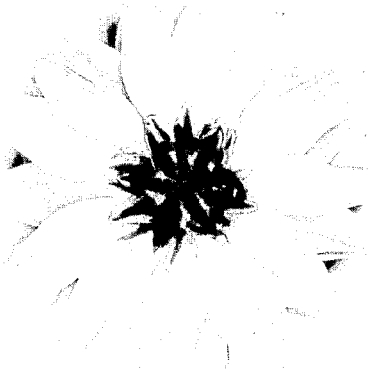

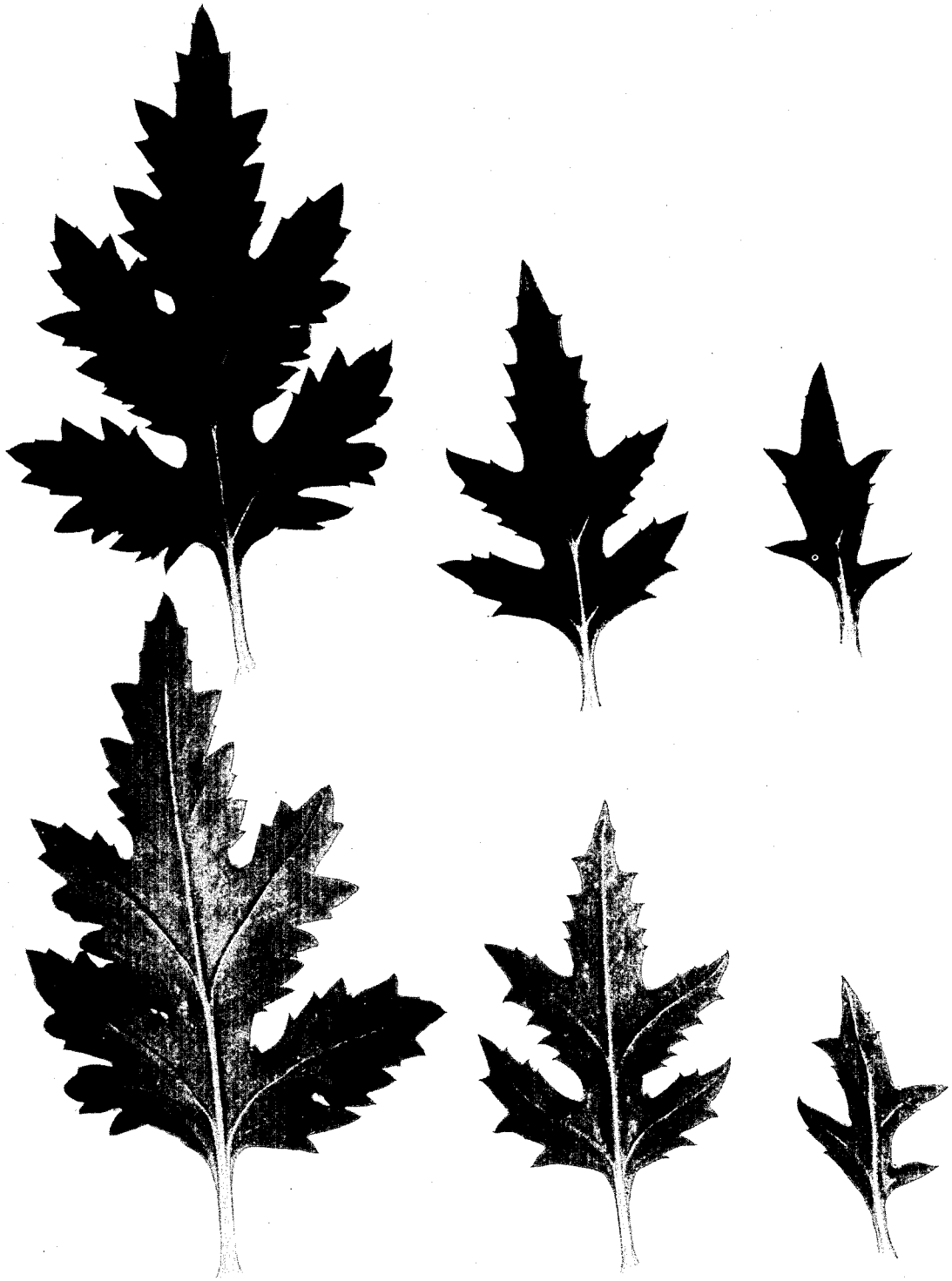

UNITED STATES PATENT AND TRADEMARK OFFICE

CERTIFICATE OF CORRECTION

PATENT NO. : PP 6,887

DATED : June 27, 1989

INVENTOR(S) : Cornelis P. VandenBerg

It is certified that error appears in the above—identified patent and that said Letters Patent is hereby corrected as shown below:

Column 1, Line 6, "Cornelius" should be "Cornelis".

Signed and Sealed this

Third Day of July, 1990

*Attest:*

HARRY F. MANBECK, JR.

*Attesting Officer*

*Commissioner of Patents and Trademarks*